US008790706B2

(12) United States Patent
Binachon

(10) Patent No.: US 8,790,706 B2
(45) Date of Patent: Jul. 29, 2014

(54) FLUID POWDER DENTIFRICE FOR THE TREATMENT OF THE GUMS, AND A CORRESPONDING PRODUCTION METHOD

(75) Inventor: Christophe Binachon, Orvault (FR)

(73) Assignee: Gencix, Orvault (FR)

( * ) Notice: Subject to any disclaimer, the term of this patent is extended or adjusted under 35 U.S.C. 154(b) by 977 days.

(21) Appl. No.: 12/411,006

(22) Filed: Mar. 25, 2009

(65) Prior Publication Data

US 2009/0246237 A1 Oct. 1, 2009

(30) Foreign Application Priority Data

Mar. 25, 2008 (FR) ...................................... 08 01595

(51) Int. Cl.
*A61K 8/11* (2006.01)
*A61K 36/00* (2006.01)

(52) U.S. Cl.
USPC ............................. 424/490; 424/1.29; 424/58

(58) Field of Classification Search
USPC .............................................. 424/53, 58, 769
See application file for complete search history.

(56) References Cited

U.S. PATENT DOCUMENTS

| 2,941,926 | A | | 6/1960 | Salzman et al. | |
|---|---|---|---|---|---|
| 5,624,906 | A | * | 4/1997 | Vermeer | 514/23 |
| 6,241,975 | B1 | * | 6/2001 | Moon et al. | 424/58 |
| 6,379,654 | B1 | | 4/2002 | Gebreselassie et al. | |
| 6,645,472 | B1 | | 11/2003 | Anderson | |
| 2002/0106335 | A1 | * | 8/2002 | Orlowski et al. | 424/53 |
| 2003/0068358 | A1 | | 4/2003 | Frater-Schroder et al. | |

FOREIGN PATENT DOCUMENTS

| DE | 199 61 936 A | 6/2001 |
|---|---|---|
| FR | 2 785 534 A | 5/2000 |
| GB | 485 188 A | 5/1938 |
| GB | 544 405 A | 4/1942 |

OTHER PUBLICATIONS

Bussadori et al., "Papain Gel: A New Chemo-Mechanical Caries Removal Agent." J Clin Pediatr Dent 30(20): 115-119, 2005.*
Dawson, "The Medicinal Properties of Papaya, *Carica papaya* L," Internet citation, http://www.siu.edu/bl/leaflets/papaya.htm, Feb. 18, 2004, p. 2.
Anonymous, "Papaya," Internet citation, http://web.archive.org/web/20071218104358/http://www.buy-vitamins-minerals.com/papaya.htm, Feb. 10, 2009, p. 2.

* cited by examiner

*Primary Examiner* — Walter Webb
(74) *Attorney, Agent, or Firm* — Muncy, Geissler, Olds & Lowe, P.C.

(57) ABSTRACT

The dentifrice powder comprises grains of ground pumice stone coated with particles of a dry extract of fruit tree leaves, in particular pawpaw leaves, and is preferably obtained by carrying out a method comprising the following steps:
producing a decoction of fruit tree leaves in water;
filtering the decoction using a sieve with a mesh of 100 μm;
adding ground pumice stone having grains with a maximum dimension of 100 μm; and
atomizing the mixture in a stream of hot air with an inlet temperature of close to 300° C. and an outlet temperature of close to 100° C.

12 Claims, No Drawings

FLUID POWDER DENTIFRICE FOR THE TREATMENT OF THE GUMS, AND A CORRESPONDING PRODUCTION METHOD

The present invention relates to a fluid powder dentifrice for treating the gums.

BACKGROUND TO THE INVENTION

Extracts from the leaves of various plants are known to have anti-inflammatory effects on the gums.

Further, leaf extracts are known to be more active when they are applied in powder form. However, powdered leaf extracts are highly hydrophilic; in fact, when a leaf extract is stored in powder form, the grains agglomerate very rapidly to form blocks that cannot be used with a toothbrush.

Furthermore, document FR-A-2 785 534 discloses a method of producing an abrasive composition for a dentifrice, comprising steps of producing an aqueous solution of grains of a calcic material and a carboxylic acid salt, and drying the solution, in particular by atomization. The composition obtained is of no use in treating the gums.

OBJECT OF THE INVENTION

One aim of the invention is to propose a fluid powder dentifrice for treatment of the gums that retains good fluidity even after prolonged storage, and also the corresponding production method.

SUMMARY OF THE INVENTION

To achieve this aim, the invention proposes a dentifrice powder comprising grains of ground pumice stone coated with particles of a dry extract of the leaf of a fruit tree, in particular the pawpaw.

It has been established that binding particles of a dry extract of pawpaw leaf on ground pumice stone grains can maintain the dentifrice powder in a fluid state even after a long storage time. Further, it has been observed that the gentle mechanical action of the grains of pumice stone has a synergistic effect with the properties of the dry extract of pawpaw leaf, such that the effects of the dentifrice produced are better than those that would be obtained with a pure active extract, or even with a mixture of a powdered active extract and a mineral or organic product in grain form.

Preferably, the grains of ground pumice stone have a maximum dimension of 100 µm [micrometer] and the majority of them have a dimension of 50 µm or less.

In order to produce this dentifrice, the invention proposes a method comprising the following steps:
  producing a decoction of pawpaw leaves in water and extracting the liquid obtained;
  adding grains of ground pumice stone to the liquid obtained;
  atomizing the mixture in a stream of hot air.

It has been shown that using pumice stone can produce an exceptionally homogeneous mixture before atomization, encouraging proper execution of this step.

DETAILED DESCRIPTION OF THE INVENTION

In accordance with a preferred implementation of the invention, dry pawpaw leaves are soaked in a weight of water equal to approximately thirty times the dry weight of the leaves. This is maintained at 90° C. for one hour, with stirring. The liquid is extracted by firstly passing the decoction through a screen with an 8 mm [millimeter] mesh, then through a filter with a 100 µm mesh.

A sample of the decoction is placed in a hot air evaporator with an inlet temperature of close to 300° C. and an outlet temperature of close to 100° C., in order to determine the quantity of dry matter contained in the final decoction.

Finely ground pumice stone having grains with a maximum dimension of 100 µm and mostly a dimension of 50 µm or less is added to the decoction in an amount of one and one-half times the weight of the dry matter contained in the decoction.

The mixture is then placed in a hot air evaporator with an inlet temperature of close to 300° C. and an outlet temperature of close to 100° C. The dispersion turbine is driven at a high rate of rotation in order to obtain a fine dispersion of the product in the drying chamber.

The dry powder obtained has been analyzed using an electron microscope; this shows that the grains of pawpaw leaf coat the grains of pumice stone to which they are attached. The powder obtained is fluid and can readily be used by moistening a toothbrush and cleaning the teeth and gums using the toothbrush in the usual manner. Experiments have shown that used in this way, the dentifrice powder has anti-inflammatory properties.

Clearly, the invention is not limited to the particular implementation described; variations may be made without departing from the scope of the invention as defined in the claims.

In particular, extraction of the active material in a single step by placing the dry pawpaw leaves to soak in approximately thirty times the weight of the dry leaves may be replaced by multi-step extraction to provide more complete extraction of the active principles contained in the pawpaw leaves. As an example, the dry pawpaw leaves are soaked first in a weight of water equal to approximately twenty times the weight of dry leaves and a first liquid extraction is carried out under the conditions described above; the pawpaw leaves are then soaked once again, this time in a weight of water equal to approximately 2.5 times the weight of the starting dry matter. This is maintained at 90° C. for ten minutes with stirring then filtered as before, firstly with a filter with an 8 mm mesh then with a filter with a 100 µm mesh. The liquid obtained is mixed with the liquid obtained during the first extraction.

Prior to evaporation, it is also possible to concentrate the liquid extract in a vacuum concentrator at 110° C. to reduce it to $1/10^{th}$ of the starting decoction.

The decoction may also be produced from fresh leaves, the quantity of water being reduced in a corresponding proportion, i.e. the fresh leaves are soaked in a weight of water equal to approximately six times the weight of the fresh leaves.

Although the preferred implementation of the method uses a quantity of pumice stone powder equal to one and one-half times the weight of the quantity of dry extract in the decoction, which corresponds to complete coating of the grains of pumice stone by the extract of pawpaw leaf, a less active dentifrice may also be produced, for example by introducing the pumice stone in an amount of two times the estimated weight of dry extract into the initial decoction.

It is also possible to produce a more active dentifrice powder by introducing the support material in an amount of only one times the weight of the dry extract in the initial decoction. Under such circumstances, electron microscope analysis reveals grains of dry extract of pawpaw leaves that are not supported by the grains of pumice stone, such that the dentifrice obtained needs to be stored in a dry place in order to prevent the grains agglomerating into unusable blocks.

Although the invention is described above in relation to an active extract obtained by a decoction of pawpaw leaves in water, the method of the invention may be carried out using other natural active extracts, for example a decoction of raspberry or tea leaves in water.

Other components, for example whitening agents, such as those described in the document mentioned in the preamble, may also be added to the dentifrice of the invention.

What is claimed is:

1. A dentifrice powder, comprising grains of ground pumice stone coated with particles of dry extract of fruit tree leaves,
    the maximum dimension of the grains being 100 μm and the majority of the grains having a dimension of 50 μm or less,
    the dentifrice powder is produced by a method comprising the following steps:
        producing a decoction of fruit tree leaves in water and extracting the liquid obtained;
        adding grains of ground pumice stone to the liquid obtained;
        atomizing the resulting mixture in a stream of air having an inlet temperature of close to 300° C. and an outlet temperature of close to 100° C.

2. A method of producing a dentifrice powder of claim 1, comprising the following steps:
    producing a decoction of fruit tree leaves in water and extracting the liquid obtained;
    adding grains of ground pumice stone to the liquid obtained;
    atomizing the mixture in a stream of hot air.

3. A method according to claim 2, wherein the support in the form of grains is added in a quantity by weight in the range from one to two times, preferably one and one-half times the quantity by weight of the dry extract in the filtered decoction.

4. A method according to claim 2, wherein the dry fruit tree leaves are soaked in a weight of water equal to thirty times the weight of the dry leaves.

5. A method according to claim 2, wherein the decoction is filtered with a sieve with a mesh of 100 μm.

6. A method according to claim 2, wherein the grains of pumice stone have a maximum dimension of 100 μm and the majority have a dimension of 50 μm or less.

7. A method according to claim 2, wherein the mixture is atomized in a stream of air having an inlet temperature of close to 300° C. and an outlet temperature of close to 100° C.

8. The dentifrice powder according to claim 1, wherein the ground pumice powder is coated only with particles of dry extract of fruit tree leaves.

9. The dentifrice powder according to claim 1, wherein the support in the form of grains is added in a quantity by weight in the range from one to two times, preferably one and one-half times the quantity by weight of the dry extract in the filtered decoction.

10. The dentifrice powder according to claim 1, wherein the dry fruit tree leaves are soaked in a weight of water equal to thirty times the weight of the dry leaves.

11. The dentifrice powder according to claim 1, wherein the decoction is filtered with a sieve with a mesh of 100 μm.

12. The dentifrice powder according to claim 1, wherein the grains of pumice stone have a maximum dimension of 100 μm and the majority have a dimension of 50 μm or less.

* * * * *